(12) United States Patent
Hartley et al.

(10) Patent No.: US 10,201,414 B2
(45) Date of Patent: *Feb. 12, 2019

(54) INTRODUCER FOR A SIDE BRANCH DEVICE

(71) Applicants: Cook Medical Technologies LLC, Bloomington, IN (US); The Cleveland Clinic Foundation, Cleveland, OH (US)

(72) Inventors: David Ernest Hartley, Wannanup (AU); John Lennon Anderson, Unley (AU); Roy K. Greenberg, Bratenahl, OH (US); Wolf Stelter, Bad Soden (DE)

(73) Assignees: Cook Medical Technologies LLC, Bloomington, IN (US); The Cleveland Clinic Foundation, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/710,255

(22) Filed: Sep. 20, 2017

(65) Prior Publication Data

US 2018/0008396 A1 Jan. 11, 2018

Related U.S. Application Data

(60) Continuation of application No. 13/181,249, filed on Jul. 12, 2011, now abandoned, which is a division of
(Continued)

(51) Int. Cl.
*A61F 2/07* (2013.01)
*A61F 2/954* (2013.01)
(Continued)

(52) U.S. Cl.
CPC ............ *A61F 2/07* (2013.01); *A61F 2/954* (2013.01); *A61F 2/89* (2013.01); *A61F 2/962* (2013.01);
(Continued)

(58) Field of Classification Search
CPC .... A61F 2/07; A61F 2/954; A61F 2/89; A61F 2/962; A61F 2002/061; A61F 2002/067; A61F 2002/075; A61F 2002/9511
See application file for complete search history.

(56) References Cited

U.S. PATENT DOCUMENTS 5,387,235 A 2/1995 Chuter
5,628,783 A 5/1997 Quiachon et al.
(Continued)

FOREIGN PATENT DOCUMENTS

EP 0508473 A2 10/1992
EP 0684022 A2 11/1995
(Continued)

OTHER PUBLICATIONS

International Search Report and Written Opinion for PCT/US2004/033566 dated May 24, 2005, 8 pages.
(Continued)

*Primary Examiner* — Jing Ou
(74) *Attorney, Agent, or Firm* — Brinks Gilson & Lione

(57) ABSTRACT

An introduction arrangement for a fenestrated or branched stent graft (13) intended for deployment into the lumen of a vessel having a blind vessel extending from it. The introducer (1) has a distal end intended to remain outside a patient in use and a proximal end with a nose cone dilator (11) and an arrangement to retain the branched stent graft distally of the nose cone dilator. A sheath (15) on the introducer extends over the branched stent graft to the nose cone dilator. An indwelling catheter (21) extends from the
(Continued)

distal end of the introducer and enters the fenestration or side arm and through to the nose cone dilator, the indwelling catheter has a guide wire (29) extending through it. The guide wire can be extended beyond the nose cone dilator in use before the sheath is withdrawn from the branched stent graft so that it can be snared from the contra-lateral artery.

20 Claims, 10 Drawing Sheets

Related U.S. Application Data application No. 10/962,763, filed on Oct. 12, 2004, now Pat. No. 8,012,193.

(60) Provisional application No. 60/601,485, filed on Aug. 13, 2004, provisional application No. 60/510,823, filed on Oct. 14, 2003.

(51) Int. Cl.
*A61F 2/962* (2013.01)
*A61F 2/06* (2013.01)
*A61F 2/95* (2013.01)
*A61F 2/89* (2013.01)

(52) U.S. Cl.
CPC ... *A61F 2002/061* (2013.01); *A61F 2002/067* (2013.01); *A61F 2002/075* (2013.01); *A61F 2002/9511* (2013.01)

(56) References Cited

U.S. PATENT DOCUMENTS

| | | | |
|---|---|---|---|
| 5,669,924 A | 9/1997 | Shaknovich | |
| 5,676,696 A | 10/1997 | Marcade | |
| 5,683,450 A | 11/1997 | Goicoechea | |
| 5,693,083 A | 12/1997 | Baker et al. | |
| 5,720,776 A | 2/1998 | Chuter et al. | |
| 5,776,142 A | 7/1998 | Gunderson | |
| 5,824,055 A * | 10/1998 | Spiridigliozzi | A61F 2/954 606/195 |
| 5,984,955 A | 11/1999 | Wisselink | |
| 6,162,246 A | 12/2000 | Barone | |
| 6,187,033 B1 | 2/2001 | Schmitt | |
| 6,206,931 B1 | 3/2001 | Cook et al. | |
| 6,325,826 B1 | 12/2001 | Vardi et al. | |
| 6,428,565 B1 | 8/2002 | Wisselink | |
| 6,524,335 B1 | 2/2003 | Hartley et al. | |
| 6,660,030 B2 | 12/2003 | Shaolian et al. | |
| 6,663,666 B1 | 12/2003 | Quiachon et al. | |
| 6,695,875 B2 | 2/2004 | Stelter et al. | |
| 6,827,726 B2 | 12/2004 | Parodi | |
| 6,858,038 B2 | 2/2005 | Heuser | |
| 6,939,370 B2 | 9/2005 | Hartley et al. | |
| 6,974,471 B2 | 12/2005 | Van Schie et al. | |
| 7,014,653 B2 | 3/2006 | Ouriel et al. | |
| 7,232,459 B2 | 6/2007 | Greenberg et al. | |
| 7,238,198 B2 | 7/2007 | Hartley et al. | |
| 7,294,147 B2 * | 11/2007 | Hartley | A61F 2/07 623/1.13 |
| 7,722,657 B2 | 5/2010 | Hartley | |
| 7,803,177 B2 | 9/2010 | Hartley et al. | |
| 7,998,186 B2 | 8/2011 | Hartley | |
| 8,012,193 B2 | 9/2011 | Hartley et al. | |
| 9,603,734 B2 * | 3/2017 | Hartley | A61F 2/954 |
| 9,808,365 B2 * | 11/2017 | Hartley | A61F 2/954 |
| 2001/0007954 A1 * | 7/2001 | Shaolian | A61F 2/07 623/1.11 |
| 2001/0012943 A1 | 8/2001 | Shaolian et al. | |
| 2001/0014823 A1 | 8/2001 | Ressemann | A61F 2/07 623/1.13 |
| 2001/0016767 A1 * | 8/2001 | Wilson | A61F 2/856 623/1.11 |
| 2001/0020184 A1 * | 9/2001 | Dehdashtian | A61F 2/07 623/1.16 |
| 2001/0037141 A1 * | 11/2001 | Yee | A61F 2/95 623/1.11 |
| 2001/0037142 A1 * | 11/2001 | Stelter | A61F 2/07 623/1.13 |
| 2002/0019665 A1 | 2/2002 | Dehdashtian et al. | |
| 2002/0045930 A1 | 4/2002 | Burg et al. | |
| 2002/0099436 A1 | 7/2002 | Thornton | |
| 2002/0143383 A1 * | 10/2002 | Parodi | A61F 2/954 623/1.11 |
| 2002/0151953 A1 * | 10/2002 | Chobotov | A61F 2/954 623/1.11 |
| 2002/0173835 A1 | 11/2002 | Bourang | |
| 2003/0088305 A1 | 5/2003 | Van Schie et al. | |
| 2003/0120332 A1 | 6/2003 | Hartley | |
| 2003/0120333 A1 * | 6/2003 | Ouriel | A61F 2/07 623/1.14 |
| 2003/0135257 A1 * | 7/2003 | Taheri | A61B 17/00234 623/1.11 |
| 2003/0153969 A1 | 8/2003 | Dehdashtian et al. | |
| 2003/0167083 A1 | 9/2003 | Lashinski et al. | |
| 2003/0181923 A1 | 9/2003 | Vardi | |
| 2003/0199967 A1 * | 10/2003 | Hartley | A61F 2/07 623/1.13 |
| 2003/0233140 A1 | 12/2003 | Hartley et al. | |
| 2004/0054396 A1 | 3/2004 | Hartley et al. | |
| 2004/0073289 A1 | 4/2004 | Hartley | |
| 2004/0082990 A1 | 4/2004 | Hartley | |
| 2004/0098079 A1 | 5/2004 | Hartley et al. | |
| 2004/0106978 A1 | 6/2004 | Greenberg et al. | |
| 2004/0138734 A1 * | 7/2004 | Chobotov | A61F 2/954 623/1.11 |
| 2004/0143286 A1 * | 7/2004 | Johnson | A61F 2/856 606/194 |
| 2005/0113905 A1 * | 5/2005 | Greenberg | A61F 2/07 623/1.16 |
| 2006/0178733 A1 | 8/2006 | Pinchuk | |

FOREIGN PATENT DOCUMENTS

| | | |
|---|---|---|
| EP | 0904745 A2 | 3/1999 |
| WO | WO98/53761 | 12/1998 |
| WO | WO99/29262 | 6/1999 |
| WO | WO99/44539 | 9/1999 |
| WO | WO01/67993 A2 | 9/2001 |
| WO | WO03/34948 | 5/2003 |
| WO | WO03/53287 | 7/2003 |
| WO | WO03/101518 | 12/2003 |
| WO | WO04/02365 | 1/2004 |
| WO | WO04/02370 | 1/2004 |
| WO | WO04/17867 | 3/2004 |
| WO | WO04/17868 | 3/2004 |
| WO | WO04/28399 | 4/2004 |

OTHER PUBLICATIONS

Restriction Requirement dated Apr. 1, 2008 for U.S. Appl. No. 10/962,763, 6 pages.
Response to Restriction Requirement dated May 23, 2008 for U.S. Appl. No. 10/962,763, 8 pages.
Office Action dated Jul. 8, 2008 for U.S. Appl. No. 10/962,763, 11 pages.
Response to Office Action dated Oct. 14, 2008 for U.S. Appl. No. 10/962,763, 10 pages.
Final Office Action dated Jan. 12, 2009 for U.S. Appl. No. 10/962,763, 7 pages.
Response to Final Office Action dated Feb. 25, 2009 for U.S. Appl. No. 10/962,763, 9 pages.
Advisory Action dated Apr. 1, 2009 for U.S. Appl. No. 10/962,763, 3 pages.
Request for Continued Examination dated Apr. 13, 2009 for U.S. Appl. No. 10/962,763, 9 pages.
Office Action dated May 8, 2009 for U.S. Appl. No. 10/962,763, 6 pages.

(56) References Cited

OTHER PUBLICATIONS

Response to Office Action dated Aug. 10, 2009 for U.S. Appl. No. 10/962,763, 9 pages.
Final Office Action dated Nov. 18, 2009 for U.S. Appl. No. 10/962,763, 8 pages.
Response to Final Office Action dated Jan. 11, 2010 for U.S. Appl. No. 10/962,763, 9 pages.
Advisory Action dated Jan. 26, 2010 for U.S. Appl. No. 10/962,763, 3 pages.
Response to Advisory Action dated Feb. 8, 2010 for U.S. Appl. No. 10/962,763, 6 pages.
Advisory Action dated Mar. 2, 2010 for U.S. Appl. No. 10/962,763, 3 pages.
Request for Continued Examination dated Mar. 24, 2010 for U.S. Appl. No. 10/962,763, 8 pages.
Office Action dated May 10, 2010 for U.S. Appl. No. 10/962,763, 9 pages.
Response to Office Action dated Jul. 16, 2010 for U.S. Appl. No. 10/962,763, 9 pages.
Final Office Action dated Oct. 25, 2010 for U.S. Appl. No. 10/962,763, 8 pages.
Examiner Interview Summary dated Nov. 22, 2010 for U.S. Appl. No. 10/962,763, 4 pages.
Pre-Brief Conference Request dated Jan. 25, 2011 for U.S. Appl. No. 10/962,763, 7 pages.
Response to Final Office Action dated Jan. 25, 2011 for U.S. Appl. No. 10/962,763, 9 pages.
Advisory Action dated Feb. 3, 2011 for U.S. Appl. No. 10/962,763, 2 pages.
Response to Advisory Action dated Feb. 14, 2011 for U.S. Appl. No. 10/962,763, 7 pages.
Advisory Action dated Mar. 2, 2011 for U.S. Appl. No. 10/962,763, 3 pages.
Pre-Brief Conference Decision dated Apr. 4, 2011 for U.S. Appl. No. 10/962,763, 2 pages.
Examiner Interview Summary dated Apr. 13, 2011 for U.S. Appl. No. 10/962,763, 5 pages.
Notice of Allowance dated Apr. 13, 2011 for U.S. Appl. No. 10/962,763, 4 pages.
Restriction Requirement dated Feb. 16, 2010 for U.S. Appl. No. 11/713,388, 6 pages.
Response to Restriction Requirement dated Mar. 11, 2010 for U.S. Appl. No. 11/713,388, 5 pages.
Office Action dated May 12, 2010 for U.S. Appl. No. 11/713,388, 12 pages.
Response to Office Action dated Jul. 16, 2010 for U.S. Appl. No. 11/713,388, 8 pages.
Final Office Action dated Oct. 26, 2010 for U.S. Appl. No. 11/713,388, 8 pages.
Response to Final Office Action dated Dec. 9, 2010 for U.S. Appl. No. 11/713,388, 6 pages.
Advisory Action dated Jan. 21, 2011 for U.S. Appl. No. 11/713,388, 3 pages.
Pre-Brief Conference Request dated Jan. 26, 2011 for U.S. Appl. No. 11/713,388, 8 pages.
Pre-Brief Conference Decision dated Apr. 5, 2011 for U.S. Appl. No. 11/713,388, 2 pages.
Notice of Allowance dated Apr. 14, 2011 for U.S. Appl. No. 11/713,388, 7 pages.
Communication for corresponding EP 04794818.7 dated Dec. 10, 2012, 3 pages.
Examination Report for corresponding EP 04794818.7 dated Jul. 1, 2013, 4 pages.
Communication for corresponding EP 04794818.7 dated Feb. 11, 2015, 3 pages.
Restriction Requirement for U.S. Appl. No. 14/469,247 dated May 28, 2015, 6 pages.
Restriction Requirement for U.S. Appl. No. 14/469,234 dated May 29, 2015, 6 pages.
Restriction Requirement for U.S. Appl. No. 13/181,285 dated Jun. 2, 2014, 6 pages.
Response to Restriction Requirement filed in U.S. Appl. No. 13/181,285 dated Oct. 2, 2014, 8 pages.
Office Action for U.S. Appl. No. 13/181,285 dated Jan. 30, 2015, 16 pages.
Response to Office Action filed in U.S. Appl. No. 13/181,285 dated Apr. 30, 2015, 10 pages.
Office Action for U.S. Appl. No. 13/181,285 dated Aug. 25, 2015, 18 pages.
Response to Office Action filed in U.S. Appl. No. 13/181,285 dated Jan. 25, 2016, 11 pages.
Response to Restriction Requirement filed in U.S. Appl. No. 14/469,247 dated Aug. 28, 2015, 9 pages.
Office Action for U.S. Appl. No. 14/469,247 dated Nov. 19, 2015, 16 pages.
Response to Restriction Requirement filed in U.S. Appl. No. 14/469,234 dated Aug. 31, 2015, 7 pages.
Office Action for U.S. Appl. No. 14/469,234 dated Oct. 21, 2015, 22 pages.
European Search Report for EP 16150466, dated Apr. 27, 2016, 6 pgs.
European Search Report for EP 16150469, dated Apr. 27, 2016, 7 pgs.
European Search Report for EP 16150468, dated Apr. 28, 2016, 8 pgs.
European Search Report for EP 16150470, dated Apr. 28, 2016, 7 pgs.
Final Office Action for U.S. Appl. No. 13/181,285 dated May 2, 2016, 20 pages.
Response to Final Office Action for U.S. Appl. No. 13/181,285 dated Aug. 2, 2016, 15 pages.
Final Office Action for U.S. Appl. No. 14/469,234 dated Jun. 28, 2016, 25 pages.
Response to Final Office Action for U.S. Appl. No. 14/469,234 dated Oct. 28, 2016, 8 pages.
Final Office Action for U.S. Appl. No. 14/469,247 dated Jul. 27, 2016, 11 pages.
Response to Final Office Action for U.S. Appl. No. 14/469,247 dated Oct. 27, 2016, 2 pages.
Notice of Allowance U.S. Appl. No. 14/469,247 dated Nov. 14, 2016, 12 pages.
Anderson, John Lennon, et al., "Endoluminal Aortic Grafting With Renal and Superior Mesenteric Artery Incorporation by Graft Fenestration," *International Society of Endovascular Specialists*, 2001, 8, pp. 3-15.
Stanley, Brendan, et al., "Fenestration in Endovascular Grafts for Aortic Aneurysm Repair: New Horizons for Preserving Blood Flow in Branch Vessels," *International Society of Endovascular Specialists*, 2001, 8, pp. 16-24.

\* cited by examiner

INTRODUCER FOR A SIDE BRANCH DEVICE

RELATED APPLICATIONS

This application is a continuation of application Ser. No. 13/181,249, filed Jul. 12, 2011, which is a divisional of application Ser. No. 10/962,763, filed Oct. 12, 2004, now U.S. Pat. No. 8,012,193, which claims the benefit of the filing date under 35 U.S.C. § 119(e) of Provisional U.S. Patent Application Ser. No. 60/601,485, filed Aug. 13, 2004 and Provisional U.S. Patent Application Ser. No. 60/510,823, filed Oct. 14, 2003, each of which are hereby incorporated by reference.

BACKGROUND

1. Technical Field

This invention relates to a medical device and more particularly to a medical device adapted for deployment of a stent graft within a human or animal body.

2. Background of the Invention

This invention will be generally discussed in relation to deployment of a stent graft into an iliac artery where it is necessary to extend a side branch from a stent graft into an internal iliac artery but it is to be understood that the invention is not so limited and may relate to any body lumen in which such a deployment is required.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

Stent grafts are used for treatment of vasculature in the human or animal body to bypass a repair or defect in the vasculature. For instance, a stent graft may be used to span an aneurism which has occurred in or associated with the iliac artery. In many cases, however, such a damaged or defective portion of the vasculature may include a branch vessel such as an internal iliac artery. Bypassing such a branch vessel without providing blood flow into it can cause problems and hence it has been proposed to provide a side branch on a stent graft which when deployed is positioned over the opening to the internal iliac artery and then another stent graft can be deployed through the side branch into the internal iliac artery to provide a blood flow path to the internal iliac artery.

Generally, when deploying an endovascular stent graft into a body lumen, it is possible to obtain access to such a body lumen from each end of the lumen where necessary, thereby facilitating placement of a device in the lumen. The internal iliac artery which extends from the common iliac artery below the aortic bifurcation is for all intents and purposes a blind vessel because there is no practical way of performing an endovascular minimally invasive procedure into that vessel other than by entry from the common iliac artery. The term blind vessel is used herein to describe such a vessel.

There have been proposals to deploy a branched stent graft into the common iliac artery via a femoral artery from a femoral incision with the branched stent graft having a side arm to extend into or at least adjacent the internal iliac artery, however, the use of such devices is very dependent upon favourable layout of the arteries and in many cases, access is extremely difficult. This invention proposes an alternative method for approaching the common iliac artery and a deployment device to enable such a method to be practised.

It is the object of this invention therefore to provide an improved deployment device or at least to provide a physician with a useful alternative.

BRIEF SUMMARY

In one form therefore, although this may not necessarily be the only or broadest form, the invention is said to reside in an arrangement for introducing a stent graft into an internal iliac artery, the arrangement having means to enable a guide wire to be extended so that it can be snared from a contra-lateral iliac artery so as to enable access to the internal iliac artery via an aortic bifurcation from the contra-lateral iliac artery.

Generally it will be seen that by the use of such a device, the deployment of a stent graft into the internal iliac is more favourable when approached from the aortic bifurcation because the geometry of the branch between the common iliac artery and the internal iliac artery is more favourable when approached from that direction.

In an alternative form, the invention is said to reside in an introducer device having arrangement for retaining a stent graft thereon, an indwelling catheter having a guide wire therethrough associated with the introducer device, the indwelling catheter extending to the proximal end of the introducer device whereby the guide wire can be advanced beyond the proximal end of the introducer device so that it can be snared.

By this arrangement, the guide wire can be extended beyond the introducer device so that it can be snared from the contra-lateral iliac artery and drawn over the aortic bifurcation and down the contra-lateral iliac artery so that the guide wire can be used to enter the internal iliac artery from over the aortic bifurcation.

Preferably the stent graft is of a type which includes a fenestration or a branch extending therefrom and the indwelling catheter extends through the fenestration or branch whereby a deployment device for a side arm can be deployed over the guide wire, once snared, to enter the fenestration or branch so that the side arm can be deployed into and extending from the fenestration or branch.

In a further form, the invention is said to reside in an introduction arrangement for a branched stent graft intended for deployment into the lumen of a vessel having a blind vessel extending therefrom; the branched stent graft having a main tubular body having a distal end and a proximal end with a main lumen therethrough, a side arm extending from the main body and having a side arm lumen therethrough and in fluid communication with the main lumen, the introduction arrangement including an introducer, the introducer having a distal end intended to remain outside a patient in use and a proximal end, the proximal end having a nose cone dilator and an arrangement to retain the branched stent graft distally of the nose cone dilator, the branched stent graft being retained on the introducer and a sheath on the introducer extending over the branched stent graft to the nose cone dilator, an indwelling catheter extending from the distal end of the introducer through an introducer lumen in the introducer to the branched stent graft, exiting from the introducer lumen at a distal end of the branched stent graft and entering the distal end of the side arm through the side arm lumen to the main lumen and extending out of the proximal end of the branched stent graft to the nose cone dilator, the indwelling catheter having a guide wire extending therethrough, whereby the guide wire can be extended beyond the nose cone dilator in use before the sheath is withdrawn from the branched stent graft.

It will be noted that by this form of introducer and branched stent graft assembly the indwelling catheter is external of the stent graft for part of its extent but during deployment it is covered by the introducer sheath.

It will be seen that by this arrangement, an introducer can be introduced into an artery such as an iliac artery and before the stent graft is exposed by retraction of the sheath the guide wire can be extended beyond the nose cone dilator to enable it to be snared from the contra-lateral iliac artery and then the guide wire can be used as will be discussed below for deployment of a leg extension or side arm stent graft into the internal iliac artery.

Preferably the nose cone dilator has a longitudinal groove thereon to receive the indwelling catheter.

The means to retain the branched stent graft on the introducer may include trigger wires extending to the distal end of the introducer and release arrangements for separate release of the proximal and distal ends of the stent graft from the introducer.

In a further form the invention is said to reside in an introducer device and a stent graft retained thereon, the stent graft comprising a tubular body and a fenestration in the tubular body, an indwelling catheter having a guide wire extending therethrough and associated with the introducer device, the indwelling catheter extending through the stent graft and the fenestration and to the proximal end of the introducer device whereby the guide wire can be advanced beyond the proximal end of the introducer device so that it can be snared and a deployment device for a side arm can be deployed over the guide wire, once snared, to enter the fenestration.

Preferably the stent graft has a proximal end and a distal end and the indwelling catheter extends outside of the stent graft distally of the fenestration and through the fenestration into the stent graft and towards the proximal end.

The fenestration can includes a side arm extending therefrom towards either the proximal or distal ends thereof. Alternatively the side arm extending from the fenestration extends inside the stent graft towards either the proximal or distal ends thereof.

The indwelling catheter can extend inside of the stent graft distally of the fenestration and through the fenestration out of the stent graft and towards the proximal end thereof.

In an alternative form the invention is said to reside in an introduction arrangement for a fenestrated graft intended for deployment into the lumen of a vessel having a blind vessel extending therefrom; the fenestrated stent graft having a main tubular body having a distal end and a proximal end with a main lumen therethrough, a fenestration in the main body, the introduction arrangement including an introducer, the introducer having a distal end intended to remain outside a patient in use and a proximal end, the proximal end having a nose cone dilator and an arrangement to retain the fenestrated stent graft distally of the nose cone dilator, the fenestrated stent graft being retained on the introducer and a sheath on the introducer extending over the fenestrated stent graft to the nose cone dilator, an indwelling catheter extending from the distal end of the introducer through an introducer lumen in the introducer to the fenestrated stent graft, exiting from the introducer lumen at a distal end of the fenestrated stent graft and entering the fenestration to the main lumen and extending out of the proximal end of the fenestrated stent graft to the nose cone dilator, the indwelling catheter having a guide wire extending therethrough, whereby the guide wire can be extended beyond the nose cone dilator in use before the sheath is withdrawn from the fenestrated stent graft.

U.S. Pat. No. 5,387,235 entitled "Endovascular Transluminal Prosthesis For Repair Of Aneurysms" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Barb and Expandable Transluminal Graft Prosthesis For Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

PCT Patent Publication No. WO98/53761 entitled "A Prosthesis and a Method of Deploying a Prosthesis" discloses an introducer for a prosthesis which retains the prosthesis so that each end can be moved independently. These features and other features disclosed in PCT Patent Publication No. WO98/53761 could be used with the present invention and the disclosure of PCT Patent Publication No. WO98/53761 is herewith incorporated in its entirety into this specification.

U.S. Pat. No. 6,524,335 and PCT Patent Publication No. WO 99/29262 entitled "Endoluminal Aortic Stents" disclose a fenestrated prosthesis for placement where there are intersecting arteries. This feature and other features disclosed in U.S. Pat. No. 6,524,335 and PCT Patent Publication No. WO 99/29262 could be used with the present invention and the disclosure of U.S. Pat. No. 6,524,335 and PCT Patent Publication No. WO 99/29262 is herewith incorporated in its entirety into this specification.

Ser. No. 10/280,486, filed Oct. 25, 2002 and published on May 8, 2003 as U.S. Patent Application Publication No. US-2003-0088305-A1 and PCT Patent Publication No. WO 03/034948 entitled "Prostheses For Curved Lumens" discloses prostheses with arrangements for bending the prosthesis for placement into curved lumens. This feature and other features disclosed in U.S. patent application Ser. No. 10/280,486, and U.S. Patent Application Publication No. US-2003-0088305-A1 and PCT Patent Publication No. WO 03/034948 could be used with the present invention and the disclosure of U.S. patent application Ser. No. 10/280,486, and U.S. Patent Application Publication No. US-2003-0088305-A1 and PCT Patent Publication No. WO 03/034948 is herewith incorporated in its entirety into this specification.

U.S. Provisional Patent Application Ser. No. 60/392,682, filed Jun. 28, 2002, U.S. patent application Ser. No. 10/447,406, filed May 29, 2003, and Published on Dec. 18, 2003, as U.S. Patent Application Publication No. US-2003-0233140-A1, and PCT Patent Publication No. WO 03/101518 entitled "Trigger Wires" disclose release wire systems for the release of stent grafts retained on introducer devices. This feature and other features disclosed in U.S. Provisional Patent Application Ser. No. 60/392,682, U.S. patent application Ser. No. 10/447,406, and U.S. Patent Application Publication No. US-2003-0233140-A1, and PCT Patent Publication No. WO 03/101518 could be used with the present invention and the disclosure of U.S. Provisional Patent Application Ser. No. 60/392,682, U.S. patent application Ser. No. 10/447,406, and U.S. Patent Application Publication No. US-2003-0233140-A1, and PCT Patent Publication No. WO 03/101518 is herewith incorporated in its entirety into this specification.

U.S. Provisional Patent Application Ser. No. 60/392,667, filed Jun. 28, 2002, and U.S. patent application Ser. No. 10/609,846, filed Jun. 30, 2003, and Published on May 20, 2004, as US Patent Application Publication No. US-2004-0098079-A1, and PCT Patent Publication No. WO 2004/028399 entitled "Thoracic Deployment Device" disclose introducer devices adapted for deployment of stent grafts particularly in the thoracic arch. This feature and other features disclosed in U.S. Provisional Patent Application Ser. No. 60/392,667, U.S. patent application Ser. No. 10/609,846, and US Patent Application Publication No. US-2004-0098079-A1, and PCT Patent Publication No. WO 2004/028399 could be used with the present invention and the disclosure of U.S. Provisional Patent Application Ser. No. 60/392,667, U.S. patent application Ser. No. 10/609,846, and US Patent Application Publication No. US-2004-0098079-A1, and PCT Patent Publication No. WO 2004/028399 is herewith incorporated in its entirety into this specification.

U.S. Provisional Patent Application Ser. No. 60/392,599, filed Jun. 28, 2002, and U.S. patent application Ser. No. 10/609,835, filed Jun. 30, 2003, and published on Jun. 3, 2004, as U.S. Patent Application Publication No. US-2004-0106978-A1, and PCT Patent Publication No. WO 2004/002370 entitled AThoracic Aortic Aneurysm Stent Graft@ disclose stent grafts that are useful in treating aortic aneurysms particularly in the thoracic arch. This feature and other features disclosed in U.S. Provisional Patent Application Ser. No. 60/392,599, U.S. patent application Ser. No. 10/609,835, and U.S. Patent Application Publication No. US-2004-0106978-A1, and PCT Patent Publication No. WO 2004/002370 could be used with the present invention, and the disclosure of U.S. Provisional Patent Application Ser. No. 60/392,599, U.S. patent application Ser. No. 10/609,835, and U.S. Patent Application Publication No. US-2004-0106978-A1, and PCT Patent Publication No. WO 2004/002370 is herewith incorporated in its entirety into this specification.

U.S. Provisional Patent Application Ser. No. 60/391,737, filed Jun. 26, 2002, U.S. patent application Ser. No. 10/602,930, filed Jun. 24, 2003, and published on Mar. 18, 2004, as U.S. Patent Application Publication No. US-2004-0054396-A1, and PCT Patent Publication No. WO 2004/002365 entitled "Stent-Graft Fastening" disclose arrangements for fastening stents onto grafts particularly for exposed stents. This feature and other features disclosed in U.S. Provisional Patent Application No. 60/391,737, U.S. patent application Ser. No. 10/602,930, and U.S. Patent Application Publication No. US-2004-0054396-A1, and PCT Patent Publication No. WO 2004/002365 could be used with the present invention and the disclosure of U.S. Provisional Patent Application Ser. No. 60/391,737, U.S. patent application Ser. No. 10/602,930, and U.S. Patent Application Publication No. US-2004-0054396-A1, and PCT Patent Publication No. WO 2004/002365 is herewith incorporated in its entirety into this specification.

U.S. Provisional Patent Application Ser. No. 60/405,367, filed Aug. 23, 2002, U.S. patent application Ser. No. 10/647,642, filed Aug. 25, 2003, and PCT Patent Publication No. WO 2004/017868 entitled "Asymmetric Stent Graft Attachment" disclose retention arrangements for retaining onto and releasing prostheses from introducer devices. This feature and other features disclosed in U.S. Provisional Patent Application Ser. No. 60/405,367, filed Aug. 23, 2002, U.S. patent application Ser. No. 10/647,642, filed Aug. 25, 2003, and PCT Patent Publication No. WO 2004/017868 could be used with the present invention and the disclosure of U.S. Provisional Patent Application Ser. No. 60/405,367, filed Aug. 23, 2002, U.S. patent application Ser. No. 10/647,642, filed Aug. 25, 2003, and PCT Patent Publication No. WO 2004/017868 are herewith incorporated in its entirety into this specification.

U.S. patent application Ser. No. 10/322,862, filed Dec. 18, 2002 and published as Publication No. US2003-0120332, and PCT Patent Publication No. WO03/053287 entitled "Stent Graft With Improved Adhesion" disclose arrangements on stent grafts for enhancing the adhesion of such stent grafts into walls of vessels in which they are deployed. This feature and other features disclosed in U.S. patent application Ser. No. 10/322,862, filed Dec. 18, 2002 and published as Publication No. US2003-0120332, and PCT Patent Publication No. WO03/053287 could be used with the present invention and the disclosure of U.S. patent application Ser. No. 10/322,862, filed Dec. 18, 2002 and published as Publication No. US2003-0120332, and PCT Patent Publication No. WO03/053287 are herewith incorporated in its entirety into this specification.

U.S. Provisional Patent Application Ser. No. 60/405,769, filed Aug. 23, 2002, U.S. patent application Ser. No. 10/645,095, filed Aug. 23, 2003, and PCT Patent Publication Number WO 2004/017867 entitled "Composite Prostheses" discloses prostheses or stent grafts suitable for endoluminal deployment. These prostheses and other features disclosed in U.S. Provisional Patent Application Ser. No. 60/405,769, filed Aug. 23, 2002, U.S. patent application Ser. No. 10/645,095, filed Aug. 23, 2003, and PCT Patent Publication Number WO 2004/017867, could be used with the present invention and the disclosure of U.S. Provisional Patent Application Ser. No. 60/405,769, filed Aug. 23, 2002, U.S. patent application Ser. No. 10/645,095, filed Aug. 23, 2003, and PCT Patent Publication Number WO 2004/017867 are herewith incorporated in its entirety into this specification.

BRIEF DESCRIPTION OF THE DRAWINGS

This then generally describes the invention but to assist with the understanding, reference will now be made to the accompanying drawings which show a preferred embodiment of the invention and a method by which the preferred embodiment of the invention may be used to deploy a stent graft into the internal iliac artery.

In the drawings.

DETAILED DESCRIPTION OF THE DRAWINGS AND THE PRESENTLY PREFERRED EMBODIMENTS

Figure 7:
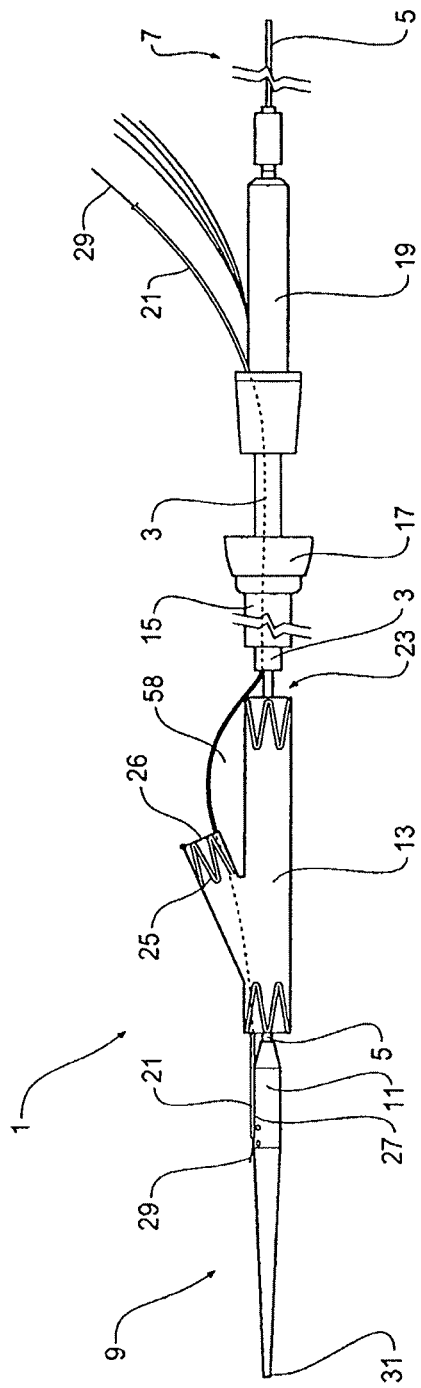
FIG. 7 shows a schematic view of a deployment device with a stent graft mounted thereon according to one embodiment of the invention.

Now looking first at FIG. 7, the introducer with a stent graft mounted onto it according to one embodiment of the present invention is shown schematically.

The introducer generally shown as 1 has an introducer catheter 3 extending over a guide wire catheter 5. The guide wire catheter 5 extends from the distal end 7 of the introducer 1 to immediately distal of the nose cone dilator 11. A branched stent graft 13 is retained at its proximal end by a retention arrangement (see FIGS. 12 and 13 for one example of a proximal retention arrangement) onto the introducer immediately distal of the nose cone dilator 11. The branched stent graft 13 is retained at its distal end by another retention arrangement (see FIGS. 14 and 15 for examples of a proximal retention arrangement) onto the introducer. A sleeve 15 operated by a sleeve manipulator 17 is mounted on the introducer catheter 3 and in the ready to deploy position the sleeve 15 extends over the branched stent graft 13 to the nose cone dilator 11. As illustrated in FIG. 7, however, the sleeve 15 is withdrawn so that the branched stent graft is exposed to show detail of the assembly. A handle 19 at the distal end of the introducer catheter 3 enables manipulation of the introducer 1. An indwelling catheter 21 enters a lumen (not shown) of the introducer catheter 3 at the handle 19 and exits from the introducer catheter 3 at the distal end 23 of the branched stent graft 13.

The branched stent graft 13 has a substantially tubular body with a main lumen through the main tubular body and a side lumen through the branch 25. The indwelling catheter 21 enters the lumen of the branch 25 from its distal end 26 and hence it passes outside the main tubular body of the branched stent graft before it enters the branch lumen. The indwelling catheter then exits from the main body adjacent the nose cone dilator and extends along the side of the nose cone dilator in a groove 27 in the nose cone dilator.

Within the indwelling catheter 21, there is a guide wire 29. This guide wire 29 can be pushed through the indwelling catheter so that it extends beyond the tip 31 of the nose cone dilator so that it can be snared as will be discussed in relation to FIGS. 1 to 6 showing one embodiment of the stent graft placement procedure. Preferably the tip 32 of the indwelling catheter is tapered around the guide wire 29 to prevent blood loss through the indwelling catheter.

Now looking at FIGS. 1 to 6, it will be seen that there is schematically illustrated a series of arteries within the human body, although as discussed earlier, the invention is not restricted to this particular application.

A descending aorta 40 extends down to an aortic bifurcation 42 from which extend common iliac arteries 44 and 46. From each of the common iliac arteries an internal iliac artery 48 and 48', respectively, extends. As discussed earlier, the internal iliac arteries 48 and 48' cannot be practically accessed from their distal ends remote from the junction with the common iliac artery.

Figure 1:
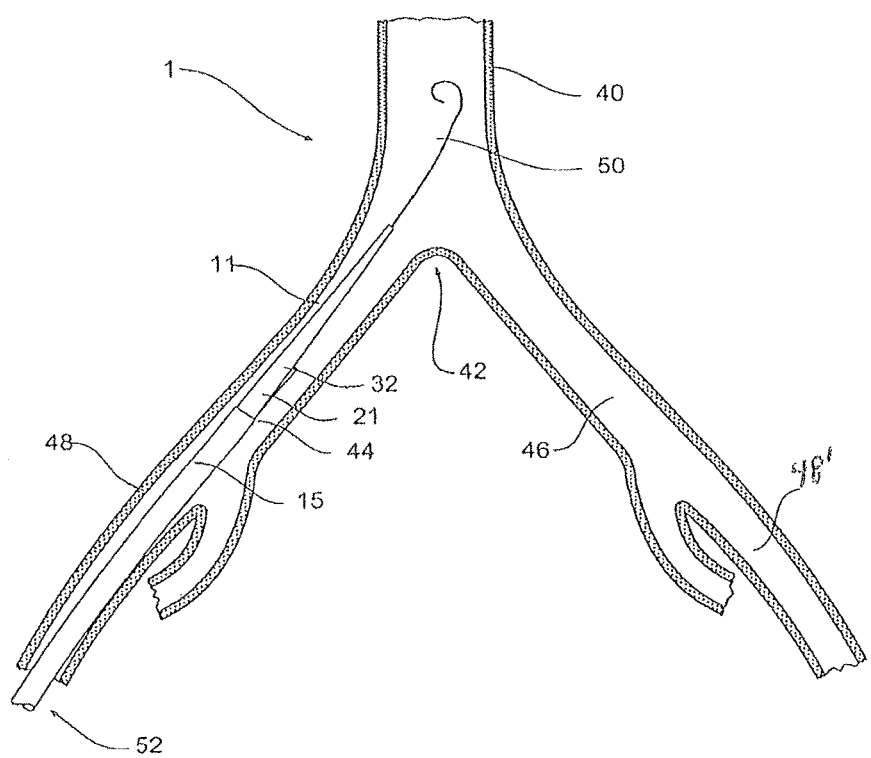
FIGS. 1 to 6 show the various stages of deployment of a stent graft on a deployment device into an iliac artery according to one embodiment of the present invention.

As shown in FIG. 1, a guide wire 50 for the deployment device 52 has been extended into a femoral artery via a femoral incision (not shown) and extended up beyond the aortic bifurcation 42 to the aorta 40. The introducer 1 has then been deployed over the guide wire with the nose cone dilator 11 extending nearly up to the aortic bifurcation. At this stage, the sleeve 15 on the deployment device extends up to the nose cone dilator 11 but has been withdrawn slightly to expose the proximal end 32 of the indwelling catheter 21.

Figure 2:
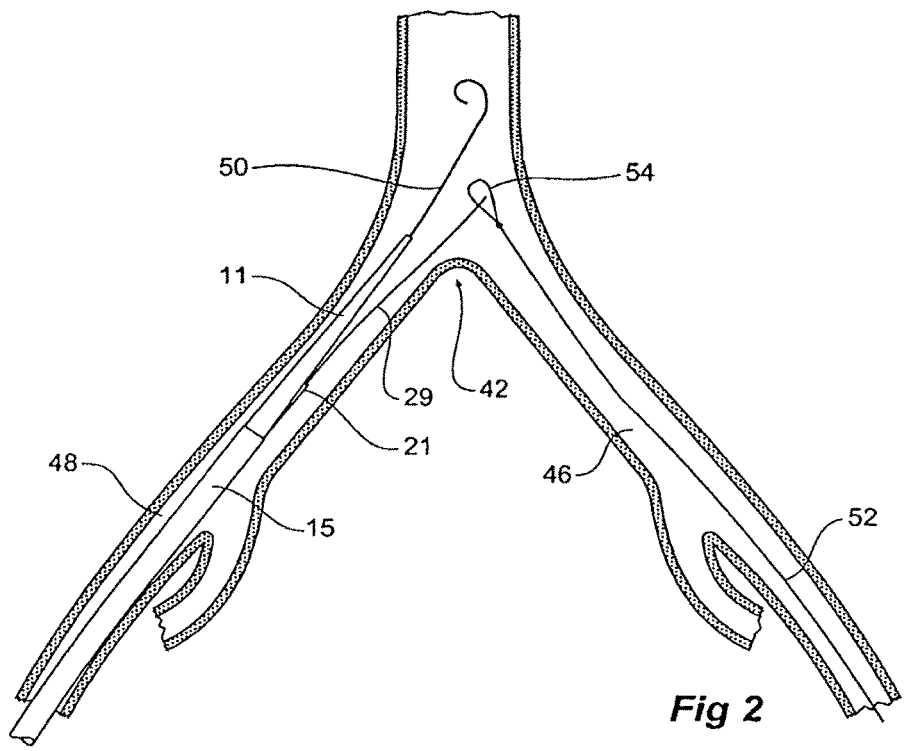

As can be seen in FIG. 2, the guide wire 29 from the indwelling catheter 21 has been extended so that it extends up beyond the aortic bifurcation but only a short distance up the aorta 40. A snare catheter 52 has been deployed via the contra-lateral iliac artery 46 and by suitable radiographic techniques the loop 54 of the snare catheter 52 is used to catch the guide wire 29.

Figure 2A:
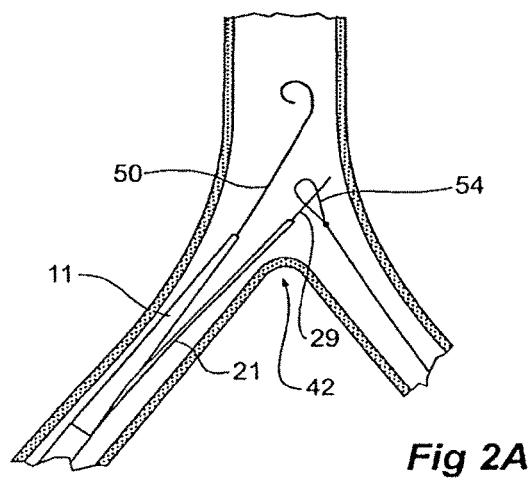

FIG. 2A shows an alternative step in the process. I this step the indwelling catheter 21 and the guide wire 29 have been advanced together to the aortic bifurcation 42 and so that the indwelling catheter 21 is beyond the nose cone dilator 11. The guide wire 29 is then advance so that it can be snared by the loop 54 of the snare catheter. By this alternative step the guide wire 29 is held more firmly and there is less likelihood that it will become entangled with the main guide wire 50.

Figure 3:
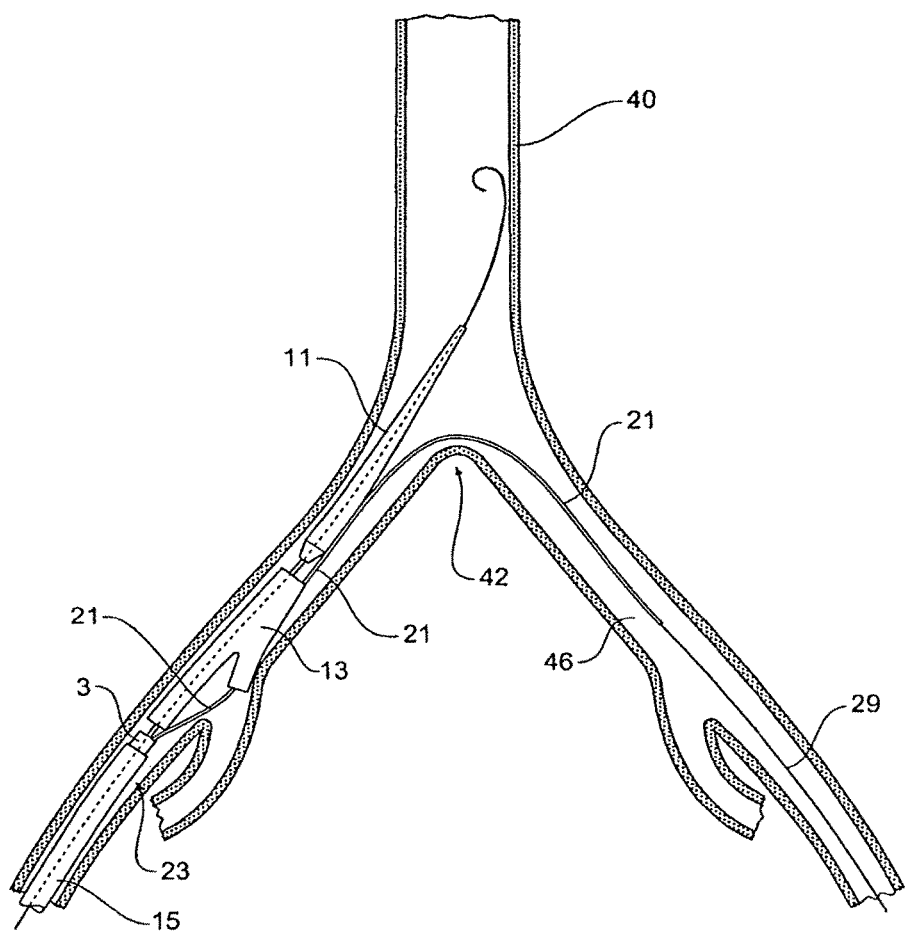

As shown in FIG. 3, the guide wire 29 has been withdrawn through the contra-lateral iliac artery 46 and the indwelling catheter 21 has been advanced over the guide wire so that it extends over the aortic bifurcation 42 and down the contra-lateral iliac artery 46. To assist this process, the sheath 15 has been withdrawn to the distal end 23 of the branched stent graft 13 so that it is just distal of the proximal end of the introducer catheter 3. At this stage the branched stent graft 13 is partially freed but is still retained by retention arrangements at at least the proximal and distal ends of the branched stent graft and is hence in an unexpanded or not fully expanded condition.

Figure 4:
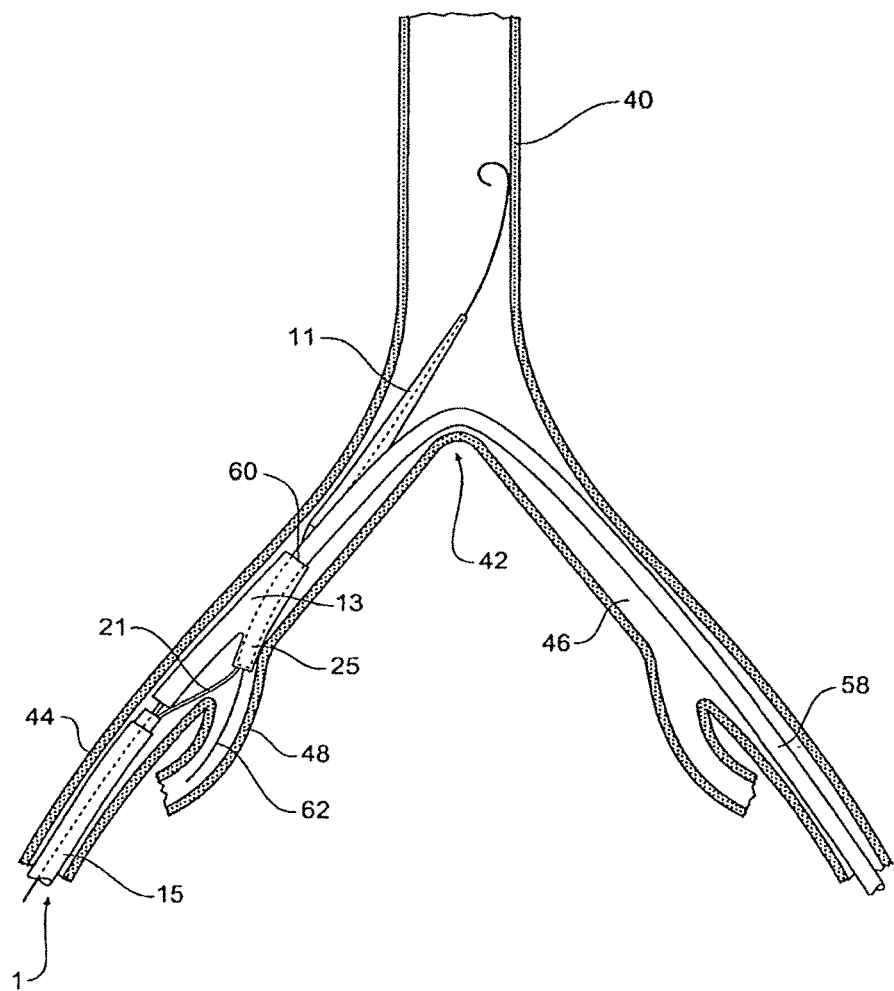

FIG. 4 shows the next stage of the process where a sheath 58 of a suitable size has been advanced over the guide wire 29 via the contra-lateral artery and indwelling catheter 21 so that it enters the proximal end 60 of the branched stent graft 13. At this stage, the indwelling catheter and guide wire 29 still extends down the iliac artery 44 on the introducer 1 so that the sheath 58 can be manipulated to successfully enter the proximal end of the branched stent graft so that it extends towards and into the branch 25 on the stent graft 13. At this stage, the indwelling catheter 21 and guide wire 19 can be withdrawn either from the contra-lateral iliac artery 46 or from the iliac artery 44 and another guide wire 62 introduced via the sheath 58. This guide wire 62 can then be manipulated so that it enters the internal iliac artery 48.

Figure 5:
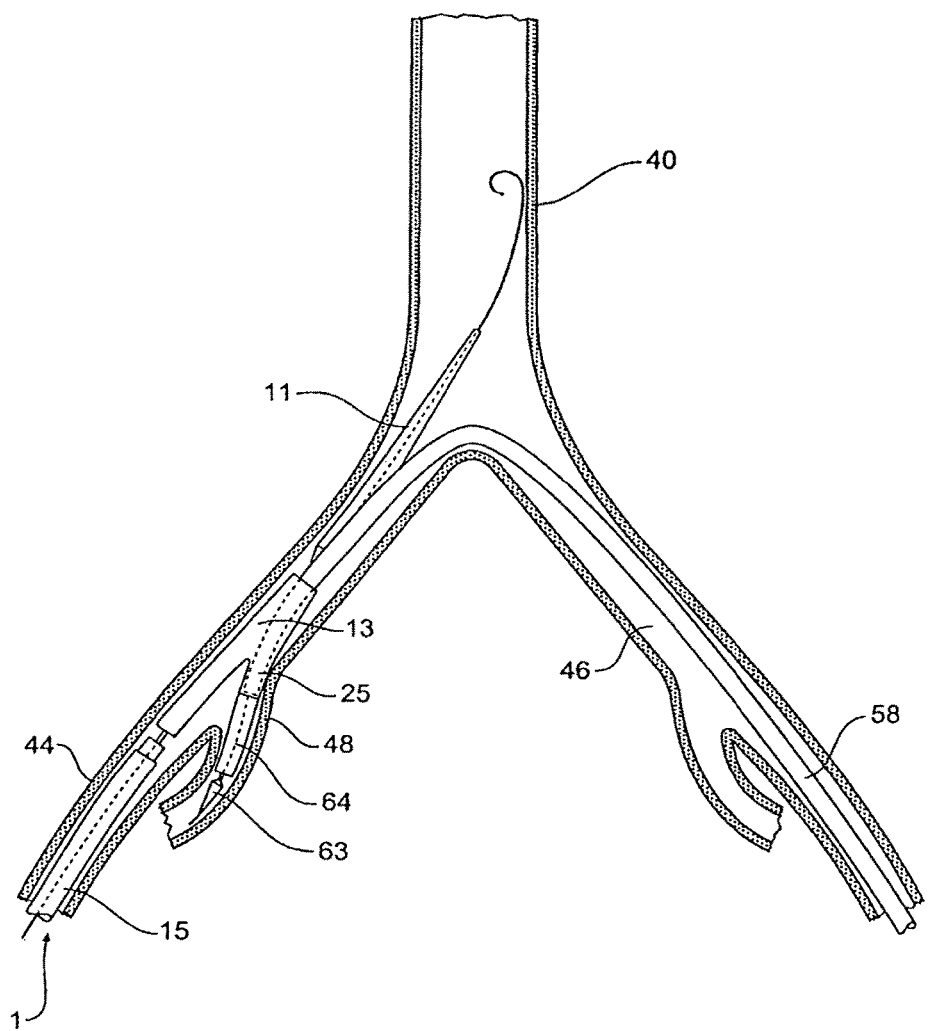

As shown in FIG. 5, a further deployment device 63 can then be introduced via the sheath 58 from the contra-lateral iliac artery 46 to extend out of the distal end of the branch 25 of the branched stent graft 13 so that a leg extension 64 can be deployed to extend from the branch 25 of the branched stent graft 13.

Figure 6:
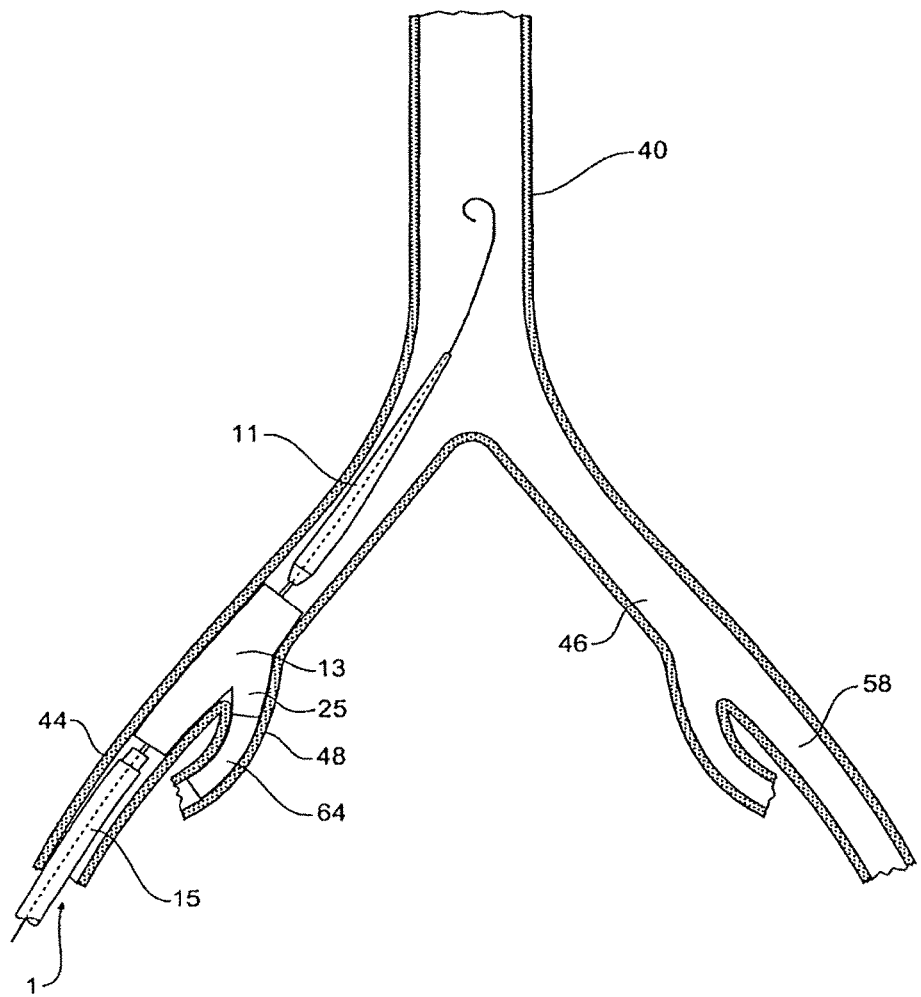

As shown in FIG. 6, the sheath 58 from the contra-lateral iliac artery 46 can then be withdrawn and the release mechanisms at each end of the stent graft 13 can be released and the leg extension 64 released so that the branched stent graft with leg extension is then deployed in the common iliac artery.

The introducer 1 can then be withdrawn although in some situations it may be desirable to leave the sleeve 15 in position so that further deployment of a stent graft into the aorta such as a bifurcated stent graft can be achieved through the sheath 15.

In summary therefore, the steps in the graft placement procedure accordingly using the device of the present invention may be as follows:

1. Deploy an introducer into a femoral artery via a femoral incision and extend the introducer up to the aortic bifurcation.
2. Withdraw the sheath to expose the proximal end of an indwelling catheter associated with the introducer.
3. Advance an indwelling guide wire through the indwelling catheter beyond the nose cone dilator of the introducer.
4. Introduce a snare catheter into the contra-lateral iliac artery via a femoral route and snare the indwelling guide wire.
5. Withdraw the indwelling guide wire through the contra-lateral iliac artery and advance the indwelling catheter around the aortic bifurcation to protect the aortic bifurcation during subsequent steps.
6. Withdraw the main sheath to expose the branched stent graft but still have the branched stent graft retained at each of its ends.
7. Deploy an auxiliary sheath over the indwelling guide wire up the contra-lateral iliac artery and into the branched stent graft via the proximal end of the branched stent graft.
8. Advance the auxiliary sheath into the short leg of the branched stent graft via the indwelling catheter guide wire or another guide wire which has been deployed through the sheath which has been placed via the contra-lateral iliac artery.
9. Remove the indwelling catheter and indwelling guide wire.
10. Advance a guide wire through the auxiliary sheath via the contra-lateral iliac artery and manipulate it into the internal iliac artery. At this stage, it may be necessary to withdraw the deployment device or rotate it slightly to guide the branch of the branched stent graft towards the internal iliac artery.
11. Advance a short leg introducer with a leg stent graft over the guide wire in the contra-lateral iliac artery and through the auxiliary sheath and into the internal iliac artery.
12. Release the proximal distal ends of the branched stent graft
13. Release the leg stent graft from the short leg introducer or balloon expand the leg stent graft.
14. Withdraw the contra-lateral iliac artery auxiliary sheath, introducer and guide wire.
15. Withdraw the main introducer.

As discussed earlier it may be necessary or desirable to leave the sheath of the main introducer and/or the main guide wire to enable deployment of further stent grafts within the aorta and aortic bifurcation.

Figure 8:
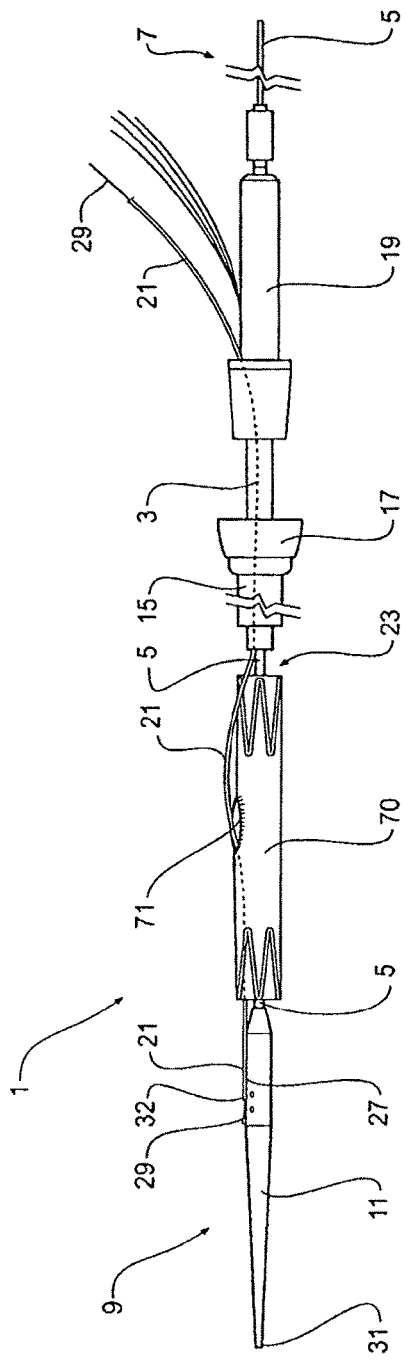
FIG. 8 shows a schematic view of a deployment device with a stent graft mounted thereon according to an alternative embodiment of the invention.
Figure 9:
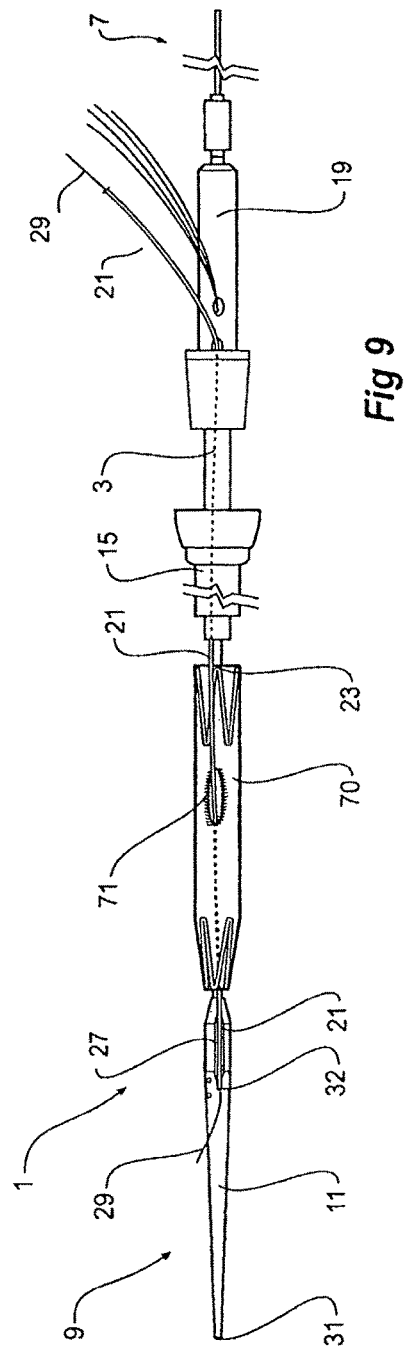
FIG. 9 shows a further schematic view of the deployment device shown in FIG. 8.

Now looking at FIGS. 8 and 9, an introducer with a stent graft mounted onto it according to an alternative embodiment of the present invention is shown schematically. The same reference numerals are used for corresponding features to those of FIG. 7.

The introducer generally shown as 1 has an introducer catheter 3 extending over a guide wire catheter 5. The guide wire catheter 5 extends from the distal end 7 of the introducer 1 to immediately distal of the nose cone dilator 11 which is at the proximal end 9 of the introducer. A fenestrated stent graft 70 is retained by a retention arrangement (not shown) onto the introducer immediately distal of the nose cone dilator 11. A sleeve 15 operated by a sleeve manipulator 17 is mounted on the introducer catheter 3 and in the ready to deploy position the sleeve 15 extends over the stent graft 70 to the nose cone dilator 11. As illustrated in FIG. 7, however, the sleeve 15 is withdrawn so that the stent graft is exposed to show detail of the assembly. A handle 19 at the distal end of the introducer catheter 3 enables manipulation of the introducer 1. An indwelling catheter 21 enters a lumen (not shown) of the introducer catheter 3 at the handle 19 and exits from the introducer catheter at the distal end 23 of the stent graft 70.

The stent graft 70 has a substantially tubular body with a main lumen through the main tubular body and a fenestration 71. The indwelling catheter 21 enters the fenestration 71 from outside the stent graft and hence it passes outside the main tubular body of the stent graft at the distal end thereof, before it enters fenestration. The indwelling catheter then passes through the main lumen of the stent graft to its proximal end and exits from the main body adjacent the nose cone dilator 11 and extends along the side of the nose cone dilator in a groove 27 in the nose cone dilator.

Within the indwelling catheter 21, there is a guide wire 29. This guide wire 29 can be pushed through the indwelling catheter so that it extends beyond the tip 31 of the nose cone dilator so that it can be snared as discussed in relation to FIGS. 1 to 6 showing a stent graft placement procedure. Preferably the tip 32 of the indwelling catheter is tapered around the guide wire 29 to prevent blood loss through the indwelling catheter.

Figure 10:
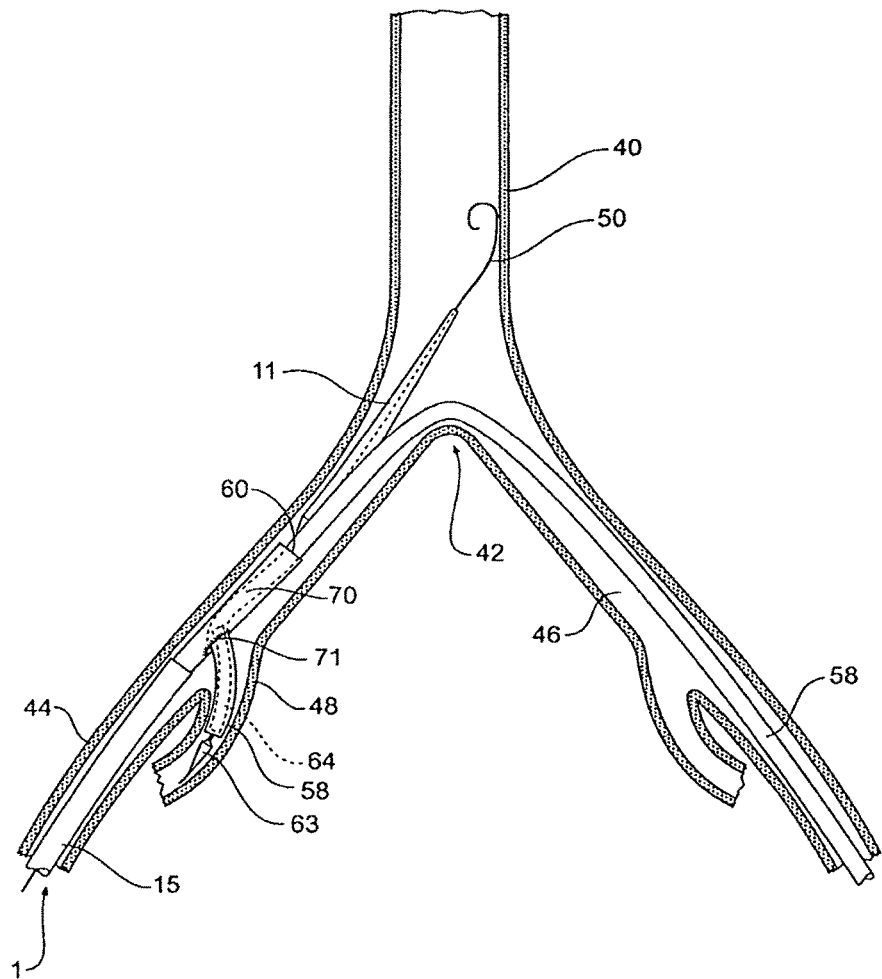
FIG. 10 shows a stage of deployment of the stent graft as shown in FIGS. 8 and 9 corresponding to the stage of deployment shown in FIG. 5 above.

FIG. 10 shows a stage of deployment of the stent graft as shown in FIGS. 8 and 9 corresponding to the stage of deployment shown in FIG. 5 above. The same reference numeral are used for corresponding features to those of FIGS. 1 to 6.

Prior to the stage shown in FIG. 10 a guide wire 50 for the deployment device 52 has been extended into a femoral artery via a femoral incision (not shown) and extended up beyond the aortic bifurcation 42 into the aorta 40. An introducer 1 has then been deployed over the guide wire with the nose cone dilator 11 extending nearly up to the aortic bifurcation. At this stage, the sleeve 15 on the deployment device extends up to the nose cone dilator but has been withdrawn slightly to expose the proximal end of the indwelling catheter 21. Next a guide wire from an indwelling catheter (not shown in FIG. 10) has been extended so that it extends up beyond the aortic bifurcation but only a short distance up the aorta 40. A snare catheter has been deployed via the contra-lateral iliac artery 46 and by suitable radiographic techniques the loop of the snare catheter has been used to catch the guide wire. The guide wire has then been withdrawn through the contra-lateral iliac artery 46 and the indwelling catheter has been advanced over the guide wire so that it extends over the aortic bifurcation 42 and down the contra-lateral iliac artery 46. To assist this process, the sheath 15 has been withdrawn to just distal of the fenestration 25 and still covering the distal end 23 of the stent graft 70. At this stage the stent graft 13 is partially freed but is still retained by a retention arrangements at the proximal end 60 of the stent graft and by the sheath at the distal end. The exposed portion of the stent graft between the proximal end and the fenestration can expand although there may be diameter reducing ties (not shown) to restrict the amount of expansion. Next a sheath 58 of a suitable size has been advanced over the guide wire 29 and indwelling catheter 21 so that it enters the proximal end 60 of the branched stent graft 70. At this stage, the indwelling catheter and guide wire 29 still extends down the iliac artery 44 on the introducer 1 so that the sheath 58 can be manipulated to successfully enter the proximal end of the branched stent graft 60 so that it extends towards and into the fenestration 71 on the stent graft 70. At this stage, the indwelling catheter 21 and guide wire 19 can be withdrawn, either from the contra-lateral iliac artery 46, or from the iliac artery 44 and another guide wire 62 introduced via the sheath 58. This guide wire 62 can then be manipulated so that it enters the internal iliac artery 48.

As shown in FIG. 10, a further deployment device 63 has then been introduced via the sheath 58 from the contralateral iliac artery 46 to extend out of the fenestration 71 of the stent graft 70. The further deployment device 63 carries a leg extension 64. The leg extension 64 can be deployed to extend from the fenestration 71 of the stent graft 70. The leg extension 64 can be a covered balloon expandable stent for instance, which is carried on a balloon in the deployment device so that it can be deployed and expanded with its proximal end retained in the fenestration and extending into the internal iliac artery 48.

Figure 11:
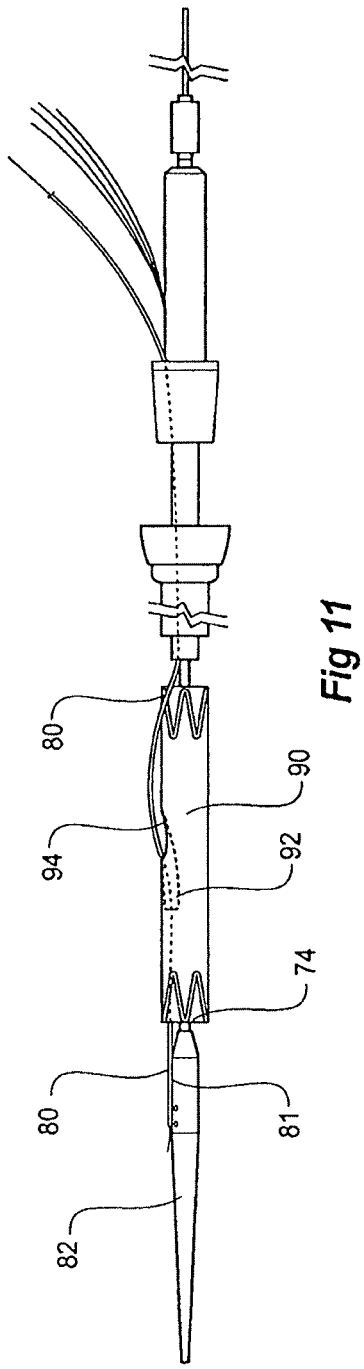
FIG. 11 shows a schematic view of a deployment device with a stent graft mounted thereon according to a further embodiment of the invention.

Now looking at FIG. 11, an introducer with a stent graft mounted onto it according to an alternative embodiment of the present invention is shown schematically.

In this embodiment the stent graft 90 has a fenestration 94 in the wall of the stent graft 90 and an internal leg extension 92 extending inwardly and toward the proximal end 74 of the stent graft 90 from the fenestration 94. The indwelling catheter 80 extends into the fenestration 94 and into the internal leg extension 92 and toward the proximal end 74 of the stent graft 90. The indwelling catheter 80 then exits from the main body adjacent the nose cone dilator 82 and extends along the side of the nose cone dilator 82 in a groove 81 in the nose cone dilator 82.

FIGS. 8 to 11 show various embodiments of the present invention in a stylised manner. It should be noted that the configuration with the main sheath withdrawn completely off the stent graft but with the indwelling catheter and guide wire in its initial position would not occur in practice.

Figure 12:
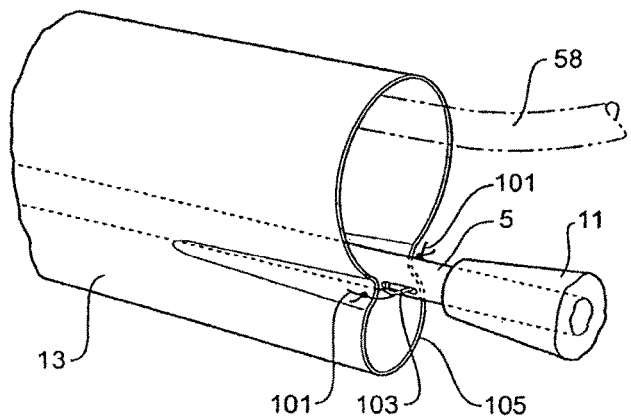
FIG. 12 shows a side view of one method of proximal retention suitable for the present invention.
Figure 13:
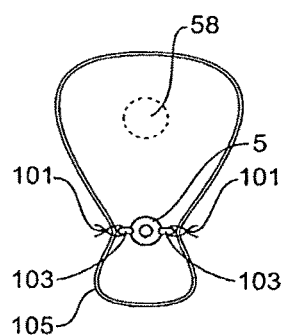
FIG. 13 shows a cross sectional view of the arrangement shown in FIG. 12.

FIG. 12 shows a side view of one method of proximal retention suitable for the present invention and FIG. 13 shows a cross sectional view of the arrangement shown in FIG. 12. The same reference numerals are used for corresponding features to those of FIG. 7 for corresponding items.

The guide wire catheter 5 extends to a nose cone dilator 11 and the proximal end of the stent graft 13 is retained onto the guide wire catheter just distal of the nose cone dilator. Retention is by means of a pair loops of suture material 101 each of which is engaged with a trigger wire 103 extending from an aperture in the guide wire catheter 5. The loops are placed so that there is formed a smaller 105 and larger fold 107 of the stent graft 13 at its proximal end. The indwelling catheter passes through the region defined by the larger fold 107 and therefore when the sheath 58 (see FIG. 4) has been advanced over the guide wire then it can more easily enter the lumen of the stent graft.

Figure 14:
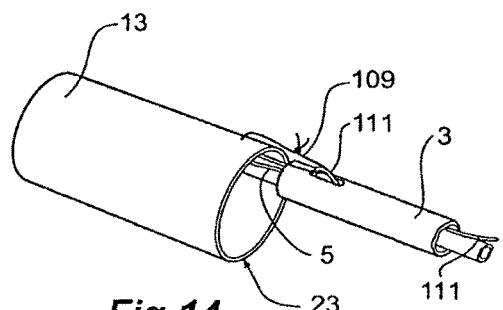
FIG. 14 shows a side view of one method of distal retention suitable for the present invention.

FIG. 14 shows a side view of one method of distal retention suitable for the present invention. The same reference numerals are used for corresponding features to those of FIG. 7 for corresponding items. In this embodiment the distal end 23 of the stent graft 13 is retained onto the guide wire catheter 5 just proximal of the deployment catheter 3 by means of a suture loop 109 engaged into the stent graft 13 and a loop of trigger wire 111 extending from the deployment catheter 3. Removal of the trigger wire 111 when required will release the distal end 23 of the stent graft 13.

Figure 15:
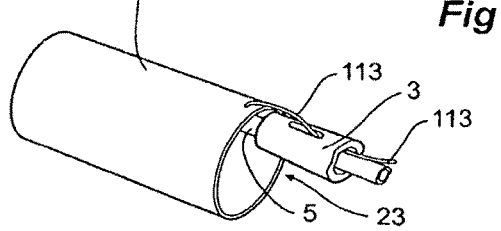
FIG. 15 shows a side view of an alternative method of distal retention suitable for the present invention.

FIG. 15 shows a side view of an alternative method of distal retention suitable for the present invention. The same reference numerals are used for corresponding features to those of FIG. 7 for corresponding items. In this embodiment the distal end 23 of the stent graft 13 is retained onto the guide wire catheter 5 just proximal of the deployment catheter 3 by means a loop of trigger wire 113 extending from the deployment catheter 3 and passing through a portion of the stent graft 13. Removal of the trigger wire 113 when required will release the distal end 23 of the stent graft 13.

Throughout this specification various indications have been given as to the scope of this invention but the invention is not limited to any one of these but may reside in two or more of these combined together. The examples are given for illustration only and not for limitation.

Throughout this specification and the claims that follow, unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A method of deploying a branched stent graft into a body vessel having a main vessel, the body vessel having a first branch vessel extending from the main vessel, a second branch vessel extending from the main vessel, a bifurcation between the first and second branch vessels, and a third vessel extending from the first branch vessel and having an ostium;
   the branched stent graft comprising a main body having a distal end, a proximal end with a main lumen therethrough, at least two main body stents, and a branch extending from the main body between the main body distal end and the main body proximal end and having an end more proximate the main body proximal end, the branch having a branch lumen therethrough in fluid communication with the main lumen, a distal open end, and a stent adjacent the distal open end;
   the method comprising:
   providing an introducer including the branched stent graft, the introducer comprising a sheath disposed over the branched stent graft, a first guide wire catheter configured to receive a first guide wire, a second guide wire catheter configured to receive a second guide wire, the second guide wire catheter disposed at least partially adjacent the first guide wire catheter, an outer catheter disposed over the first guide wire catheter and the second guide wire catheter and disposed within the sheath,
   wherein the first guide wire catheter has a portion that extends from a distal portion of the introducer to the distal open end of the branch, a portion that extends outside of and at least partially along the main body of the branched stent graft, a portion that extends into the distal open end of the branch and through the branch lumen to the main lumen, and toward the proximal end of the branched stent graft;

advancing the first guide wire across the bifurcation such that a portion of the first guide wire is disposed in one of the first and second branches and another portion is disposed in the branch lumen of the branched stent graft;

advancing the second guide wire into the first branch vessel and past the bifurcation;

advancing the second guide wire catheter of the introducer with the branched stent graft over the second guide wire;

aligning the branched stent graft such that the distal opening of the branch is above the third branch ostium;

at least partially removing the sheath from the branched stent graft to expose the branched stent graft;

advancing an auxiliary sheath over the first guide wire and into the second branch vessel, over the bifurcation and into the branch of the branched stent graft;

advancing a third guide wire through the auxiliary sheath and into the branch of the branched stent graft and into the third branch vessel;

advancing a second introducer having leg extension over the third guide wire, through the auxiliary sheath, through the proximal end of the main body, through the lumen of the main body, into the branch of the branched stent graft, and at least partially into the third branch vessel;

deploying the leg extension at least partially in the branch lumen and at least partially in the third branch vessel;

expanding the leg extension to engage the branch and the third branch vessel;

releasing the distal end of the branched stent graft from the introducer.

2. The method of claim 1, wherein the first guide wire is introduced into the introducer and the branched stent graft by way of the first guide wire catheter.

3. The method of claim 2, wherein the first guide wire is advanced through the first guide wire catheter.

4. The method of claim 1, including introducing a snare to snare the first guide wire and place it across the bifurcation.

5. The method of claim 1, wherein the second introducer has a tapered nose cone.

6. The method of claim 5, wherein the second introducer comprises a balloon.

7. The method of claim 6, wherein the leg extension comprises a balloon expandable stent.

8. The method of claim 1, wherein the step of releasing the distal end of the branched stent graft comprises withdrawing a wire from the distal end of the branched stent graft.

9. The method of claim 1, further comprising retracting the second guide wire.

10. The method of claim 1, further comprising retracting the second guide wire catheter.

11. The method of claim 1, wherein the introducer comprises a nose cone dilator comprising a longitudinal groove.

12. The method of claim 11, wherein the first guide wire is advanced through the longitudinal groove.

13. A method of deploying a branched stent graft into a first common iliac artery of an abdominal aorta below a point of bifurcation between the first common iliac artery and a second common iliac artery and at a junction of the first common iliac artery and an internal iliac artery having an internal iliac ostium, the method comprising:

providing a branched stent graft comprising a main body having a distal end, a proximal end with a main lumen therethrough, and at least two main body stents, a branch extending from the main body between the main body distal end and the main body proximal end and having an end more proximate the main body proximal end, the branch having a branch lumen therethrough in fluid communication with the main lumen, a distal open end, and a stent adjacent the distal open end;

providing a delivery device including the branched stent graft, the delivery device comprising a retractable sheath disposed over the branched stent graft, a first guide wire catheter, a second guide wire catheter at least partially adjacent the first guide wire catheter, an outer catheter disposed over the first guide wire catheter and the second guide wire catheter and disposed within the retractable sheath, wherein the first guide wire catheter has a portion that extends from a distal portion of the delivery device to the distal open end of the branch, a portion that extends outside of and at least partially along the main body of the branched stent graft, a portion that extends into the distal open end of the branch and through the branch lumen to the main lumen, and a portion that extends through the main lumen to a nose cone;

advancing a first guide wire across the aortic bifurcation such that a portion of the first guide wire is disposed in the first common iliac artery and extends into the first guide wire catheter and another portion is disposed in the second common iliac artery;

advancing a second guide wire into the first common iliac artery and extending it past the aortic bifurcation;

advancing the second guide wire catheter of the delivery device with the branched stent graft over the first guide wire;

aligning the branched stent graft such that the distal opening of the branch is above the internal iliac ostium;

at least partially removing the retractable sheath from the branched stent graft to expose the branched stent graft;

advancing an auxiliary sheath over the first guide wire and into the second common iliac artery, over the bifurcation, through the proximal end of the branched stent graft, and into the branch of the branched stent graft;

advancing a third guide wire through the auxiliary sheath, into the branch of the branched stent graft, and into the internal iliac artery;

advancing a leg extension over the third guide wire, through the auxiliary sheath, through the proximal end of the main body, through the lumen of the main body, through the branch of the branched stent graft, and at least partially into the internal iliac artery;

expanding the leg extension such that a first end of the leg extension resides in the branch of the branched stent graft and a second end of the leg extension resides in the internal iliac artery; and releasing the distal end of the branched stent graft from the delivery device.

14. The method of claim 13, further comprising the step of retracting the second guide wire catheter.

15. The method of claim 13, further comprising snaring the first guide wire.

16. The method of claim 13, wherein the step of partially removing the retractable sheath from the branched stent graft comprises exposing the branch of branched stent graft.

17. The method of claim 13, further comprising retracting the second guide wire.

18. The method of claim 13, further comprising retracting the second guide wire catheter.

19. The method of claim 13, wherein the delivery device comprises a nose cone dilator comprising a longitudinal groove.

20. The method of claim 19, wherein the first guide wire is advanced through the longitudinal groove.

* * * * *